US00PP26771P3

(12) United States Plant Patent
Maillard et al.

(10) Patent No.: US PP26,771 P3
(45) Date of Patent: May 31, 2016

(54) NECTARINE TREE NAMED 'NECTAFLASH'

(50) Latin Name: ***Prunus persica* (L.) Batsch var. *nucipersica***
Varietal Denomination: NECTAFLASH

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 98 days.

(21) Appl. No.: 13/999,807

(22) Filed: Mar. 24, 2014

(65) Prior Publication Data

US 2015/0271967 P1 Sep. 24, 2015

(51) Int. Cl.
*A01H 5/00* (2006.01)

(52) U.S. Cl.
USPC ..... Plt./190

(58) Field of Classification Search
USPC ..... Plt./190
See application file for complete search history.

(56) References Cited

PUBLICATIONS

Delivery bill from ASF to Euro Pépinières dated Sep. 14, 2015; with English machine translation (3 pages).
Redacted delivery estimate from ASF to Les Vergers d'Ouiveillan dated Sep. 9, 2015; with English machine translation (3 pages).
Redacted delivery estimate from Euro Pépinières to FLPO Exploitation (Les Vergers d'Ouiveillan) dated Sep. 9, 2015; with English machine translation (3 pages).
Redacted contract between ASF and Les Vergers d'Ouiveillan dated Nov. 18, 2015; with English machine translation (10 pages).
France plant application for NECTARFLASH dated Nov. 27, 2012; with English machine translation (2 pages).
European Community plant application for NECTARFLASH No. 2012/2703 dated Nov. 27, 2012; with English machine translation (2 pages).
European Community Official Gazette excerpt for NECTARFLASH dated Feb. 15, 2013; in English (12 pages).
Information sheet for NECTARFLASH dated Jul. 28, 2014; with English machine translation (2 pages).
Information table for NECTARFLASH (Oct. 8, 2013); with English machine translation (5 pages).

*Primary Examiner* — Annette Para
(74) *Attorney, Agent, or Firm* — Westerman, Hattori, Daniels & Adrian, LLP

(57) ABSTRACT

A new and distinct variety of yellow nectarine tree denominated 'NECTAFLASH' has fruits with high eating quality and very long shelf life without alteration before and after harvesting, with a semi-sweet yellow flesh, with a red pigmentation near the fruit's skin, and an attractive luminous and homogenous skin with a high percentage of dark red blush on skin surface, on an orange background

2 Drawing Sheets

Botanical classification: *Prunus persica* (L.) Batsch var. *nucipersica.*

Variety denomination: 'NECTAFLASH'.

BACKGROUND OF THE NEW VARIETY

The present invention relates to a new and distinct variety of yellow nectarine tree, *Prunus persica* (L.) Batsch var. *nucipersica*, which has been given the variety denomination 'NECTAFLASH'.

This new tree produces fruits with a long shelf life without alteration both on the tree after growth completion and after harvesting, very good eating quality, clingstone orange yellow flesh fruits, generally with a red pigmentation near the skin, for fresh market at the end of June or early in July in the Pyrénées-Orientales department, France.

ORIGIN OF THE VARIETY

The 'NECTAFLASH' yellow nectarine tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

'NECTAFLASH' was provisionally designated, tested and genetically identified by a genetic profile, under number 03.30W.109.11.

The 'NECTAFLASH' variety results from a pollinated cross between a yellow nectarine tree named 'NECTABANG' (U.S. Plant Pat. No. 22,494) which was used as the seed parent and the yellow nectarine tree named 'NECTABELLE' (U.S. Plant Pat. No. 21,140) which was uses as the pollen parent.

The 'NECTAFLASH' variety was obtained by hybridizing and propagated by grafting on a "INRA® GF677" rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'NECTAFLASH' yellow nectarine tree blooms at the beginning of February or early in March near Elne in the Pyrénées-Orientales department, France. More particularly, in 2012, it bloomed between $9^{th}$ and $15^{th}$ of March, in 2013 between February $7^{th}$ and February $17^{th}$. The blooming period is considered medium. However, it was observed that its late date of blooming seems to be highly dependent on climatic conditions.

The first fruit of 'NECTAFLASH' ripens generally at the end of June or early in July. The time of maturity for consumption is considered early to medium. However, it was observed that its date of maturity seems to be highly dependent on climatic conditions.

DESCRIPTION OF THE DRAWINGS

In the accompanying drawing, which are as nearly true as it is reasonably possible to make in a color illustration of this type.

Figure 1:
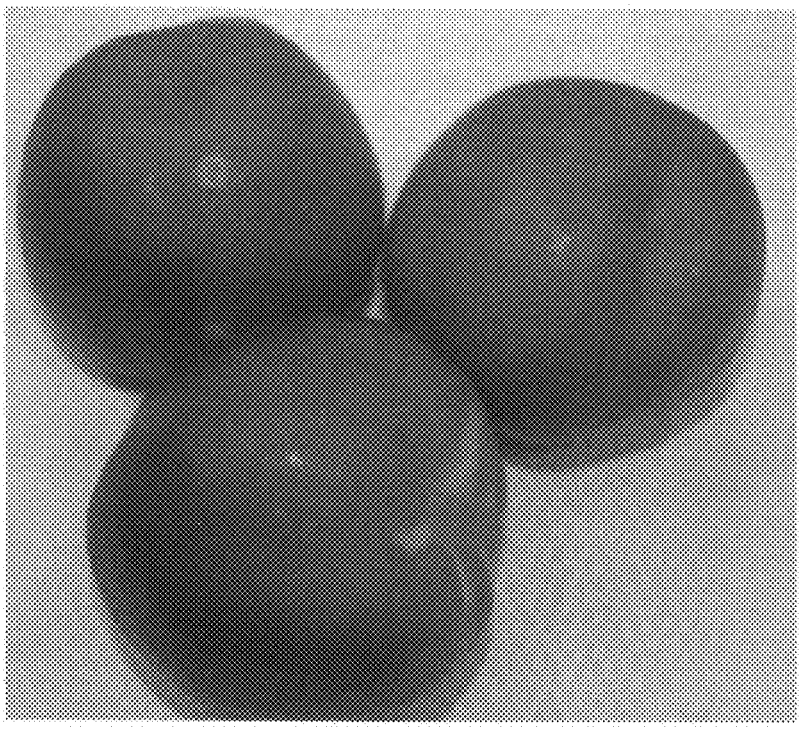
FIG. 1 is a color photograph that shows a close view of three typical specimens of the fruits of the new variety 'NECTAFLASH' at ripening time.
Figure 2:
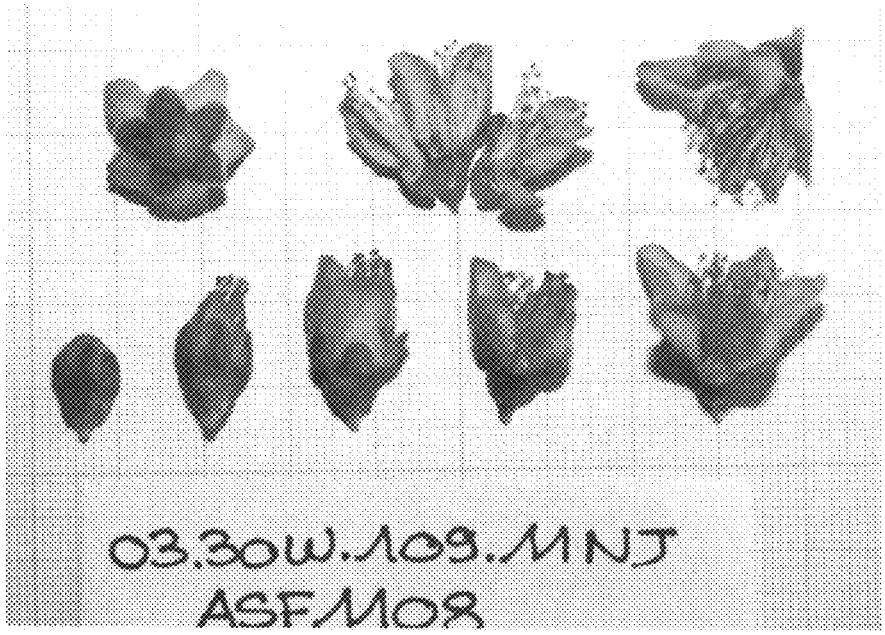
FIG. 2 is a color photograph which depicts the flower buds at different development stages, and the reverse and side view of the flower and the reproductive organs with petals removed, of the new variety.
Figure 3:
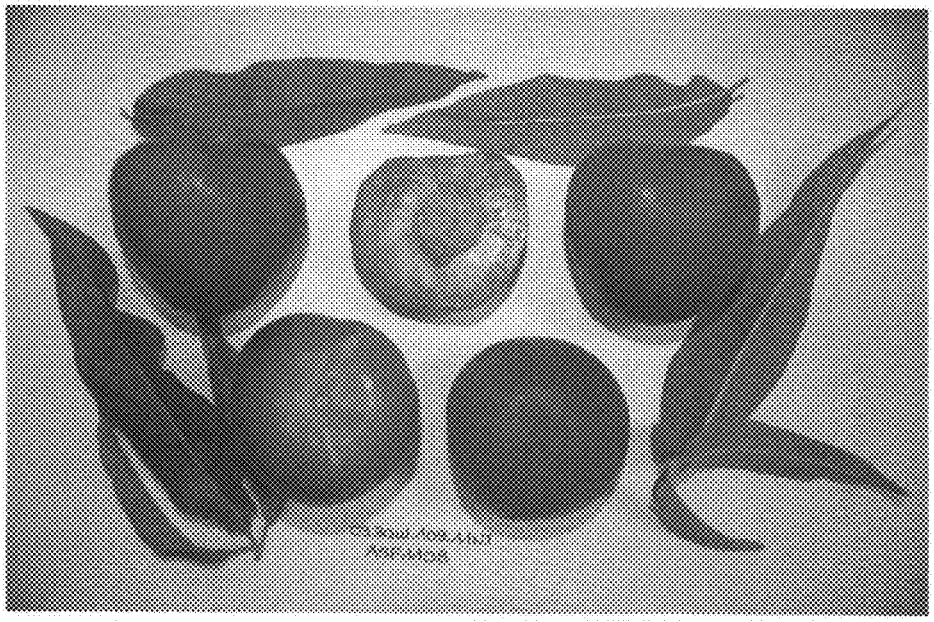
FIG. 3 is a color photograph which shows five typical specimens of the fruit, one of them having been cut in half with the pit being left in one of the halves for depicting leaves, fruit flesh, and stone of the new variety.
Figure 4:
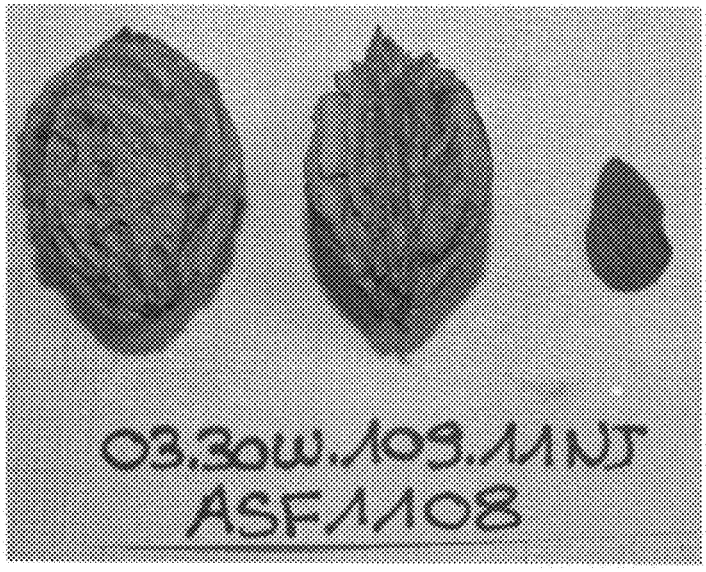
FIG. 4 is a color photograph showing different views of the stone of the new variety and the kernel of the stone.

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'NECTAFLASH' is high, due to fruit very long shelf life without alteration after harvesting.

Trees are vigorous and large stature half-standing in a semi-flared to semi-upright out aspect. The anthocyanic coloration of flowering shoot is present excluding brushwood side away from sun. The time of beginning of flowering is considered medium. More particularly, the flowering begins at the beginning of February or early in March. The type of flower is non showy with small petal size. Petals are purple pink. Leaf glands are present and round. The fruit flesh is orange yellow with a red pigmentation near the skin. The fruit skin is very thick, with a luminous dark red blush on an orange background. The stone is clingstone and his size is medium. Fruit taste is semi-sweet, very aromatic and with a high level of sugars.

Compared to 'NECTABANG' variety (U.S. Plant Pat. No. 22,494), which is the female parent, 'NECTAFLASH' variety blooms 2 days earlier and the fruits of 'NECTAFLASH' variety ripen 7 days later than 'NECTABANG' fruits. The maturity of 'NECTAFLASH' variety is considered early to medium. The fruits color of the new 'NECTAFLASH' variety is dark red on 95 to 100 percent of the skin, whereas 'NECTABANG' fruits are colored in a dark red on 95 percent of the skin. Moreover, the 'NECTAFLASH' fruits form is round and homogenous whereas 'NECTABANG' fruits form is round but slightly asymmetrical. Moreover, the fruits of the new variety are more sugary than 'NECTABANG' fruits. Indeed, the Brix of the 'NECTAFLASH' fruits is between 14 and 16 degrees. In comparison, the Brix of 'NECTABANG' fruits is approximately 12 degrees. Concerning now stones of the 'NECTABANG' fruits, some of them are split. It is not the case for the stones of the new variety.

Compared to its male parent, which is 'NECTABELLE' (U.S. Plant Pat. No 21,140) yellow nectarine tree, the new variety 'NECTAFLASH' ripens generally 3 weeks later and blooms approximately at the same period or slightly earlier. Both varieties have a non-showy type of flowers, with small petals, and circular leaf glands. The fruit size of 'NECTAFLASH' (homogenous 2A-A) is higher than the fruit size of 'NECTABELLE' (homogenous A). The color of 'NECTAFALSH' fruits can be considered luminous purple dark red on 95 to 100% of the fruit skin on an orange background covering at the most 5% of the skin. In comparison, fruits of 'NECTABELLE' are colored with a bright red on an orange background.

Compared to 'NECTAFUN' (U.S. Plant Pat. No. 24,094) variety, 'NECTAFLASH' variety blooms 2 days later. Moreover, the fruits of 'NECTAFLASH' variety ripen approximately 5 days earlier than the fruits of 'NECTAFUN'. The fruits color of the new 'NECTAFLASH' variety is dark red on 95 to 100 percent of the skin. On the contrary 'NECTABANG' fruits are colored in a bright red on 100 percent of the fruits skin.

DETAILED DESCRIPTION

Referring more specifically to the pomological details of this new and distinct variety of yellow nectarine tree, the following was observed on trees in their third growing season (second year of production) under the ecological conditions prevailing at the orchards located near the town of Elne, Pyrénées-Orientales departement, France. All observations have been done on rootstock cultivars. Used rootstocks were "INRA® GF677" trees. All major color code designations are by reference to The R.H.S. Color Chart (Fourth Edition) provided by The Royal Horticultural Society of Great Britain.

Tree:

*Size.*—Generally. — Considered large. The tree size the first year was approximately 250 cm. The tree was pruned during each following dormant season to a height of approximately 250 cm. Current season shoots growth could reach 60 to 80 cm. The tree size from the second year (second and next years) reached a final height between 310 and 330 cm including current season shoots length. The tree size is consistently reduces to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered strong.

*Productivity.*—Very productive and regular, every year. Fruit set is spaced by thinning to develop the remaining fruit into the desired market sized fruit. The number of the fruit set varies with the prevailing climatic conditions and cultural practices employed during the bloom period, and is therefore not distinctive of the present variety.

*Bearer.*—Very regular. The fruit distribution is considered homogenous on mixed branches. Thinning of 1 fruits out of 3 was necessary for the tree valorisation. Thinning was necessary every year during the years of observation.

*Form.*—The 'NECTAFLASH' variety has naturally a semi-flared to semi-upright shape.

*Hardiness.*—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. No damages were caused by ascertained temperatures as low as −12 degrees Celsius in winter. The tree was also very resistant to frosty springtime weather.

Trunk:

*Diameter.*—Approximately between 5.5 and 6.5 centimeters in diameter when measured at a distance of approximately 30.0 centimeters above the soil level.

*Bark texture.*—Considered rough, with lenticels.

*Lenticels.*—Numerous lenticels are present. The lenticels range in size from approximately 20.0 to 40.0 millimeters in width, and about 15.0 millimeters in height.

*Lenticel color.*—The outside of lenticels has a silver-grey color (RHS Grey 201 C), whereas the inside is considered brown (RHS Greyed Orange 166 B).

*Bark coloration.*—The bark has a silver-grey color (RHS Grey 201 C or RHS Black 202 C) that is slightly darker that the lenticels color.

Branches:

*Size.*—Mature branche's and current season shoots are considered medium for the variety.

*Diameter.*—Average as compared to other nectarine varieties. The current season shoots have a diameter from 5.0 to 7.0 millimeters, and mature branches have a diameter from 12.0 to 18.0 millimeters.

*Surface texture.*—Average, wood which is several years old has no furrowed appearance.

*Crotch angles.*—Primary branches are considered variable, but the crotch angles are generally between 50 degrees and 60 degrees from the horizontal axis.

*Current season shoots.*—Internode length: Generally between 25.0 and 35.0 millimeters. Color of mature branches: Considered brown (RHS Grey Brown 199 A to RHS Grey Brown B).

*Current seasons shoots.*—Color. — The color of new shoot tips is considered pale yellow-green (RHS Yellow Green 144 A to RHS Yellow Green C) on lower part of new shoot tips, whereas the upper part is darker and colored in brown-purple to brown red (RHS Greyed Purple Group 187 A to RHS Greyed Purple Group 187 B or RHS Greyed Red 182 A), depending on the level on the tip.

Leaves:

*Size.*—Considered medium to large for the species. The ratio leaf length/leaf width is 3.71. Leaf length: Approximately 122.0 to 162.0 millimeters with leaf petiole. The medium length is about 140.8 millimeters without leaf petiole. Leaf width: Approximately 31.0 to 45.0 millimeters. The medium width is 38.0 millimeters.

*Leaf base shape.*—Concave.

*Leaf form.*—Lanceolate.

*Leaf tip form.*—Short and pointed.

*Leaf color.*—Upper leaf surface. — Dark Green (RHS Green 137 A to RHS Green 137 B). Lower surface. — A lighter green (RHS Green 137 C) than the upper leaf surface color.

*Leaf texture.*—Smooth and glabrous.

*Leaf venation.*—Pinnately veined.

*Mid-vein.*—Color. — Light green, almost yellow (RHS Yellow Green 150 D). The color may evolve with maturity.

*Leaf margins.*—Slightly undulating.

*Form.*—Considered slightly dentate.

*Uniformity.*—Leaves are isolated or grouped by 2 or 3. In this last case, one leaf of normal size is found with one or two smaller leaves (at least 50% smaller).

*Leaf petioles.*—Size. — Considered medium to small. Length. — About 0.8 to 1.2 millimeters. Diameter. — About 1.5 millimeters.

*Petioles color.*—Upper petiole surface. — Light green (RHS Yellow Green 144 C to RHS Yellow Green 144 D). Lower surface. — Light green (RHS Yellow Green 150 C).

*Leaf glands.*—Size. — Considered small to medium. Their length is about 1.5 millimeters and their width is about 1.0 millimeter. Number. — Generally 2 glands per leaf. Type. — Round. Color. — On young leaves, leaf glands color is considered a light green (RHS Green 144 B to RHS Green 144 A). On older leaves, leaf glands color turns to a dark brown (RHS Grey Brown 199 A to RHS Grey Brown 199 B). Margins. — Smooth.

*Leaf stipules.*—Generally. — No leaf stipules were observed. But as seen in the characteristic relative to the leaves uniformity, it is possible to find leaves by groups of 2 or 3, with a normal-size leaf and smaller ones.

Flowers:

*Flower buds.*—Generally. — At pre-floral stage of development, the floral buds are conic in form with a round tip. Their form is evolving until blooming, with variables dimensions. Just before blooming, floral buds are approximately 7.0 to 8.0 millimeters wide and approximately 18.0 to 19.0 millimeters long. Color. — This characteristic is dependent upon the proximity to bloom. At pre-floral stage of development, the bottom of the flowers buds, formed by the sepals, is of purple-brown color (RHS Greyed Purple 183 A to RHS Greyed Purple 183 C or RHS Greyed Purple 187 B or RHS Grey Brown Group 199 A near the base). The corolla, formed by the petals, is generally of medium pink color (RHS Red Purple 65 B or RHS Red Purple 69 C). Petals color shows an evolution until the end of flowering.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins at the beginning of February or early in March. The first bloom was observed on Mar. 9, 2012.

*Blooming time.*—Considered medium in relative comparison to other commercial nectarine cultivars grown in the Pyrénées-Orientales departement, France. The date of full bloom is observed generally at the middle of the blooming period. The date of bloom varies slightly with climatic conditions and cultural practices. Thus the full bloom was observed in 2012, from Mar. $9^{th}$ until Mar. $15^{th}$ and from Feb. $7^{th}$ to Feb. 17, 2013.

*Duration of bloom.*—Approximately 7 to 11 days. This characteristic varies slightly with the prevailing climatic conditions.

*Flower type.*—The variety is considered to have a non-showy type flower.

*Flower size.*—Considered small. Flower diameter at full bloom is approximately 17.0 to 20.0 millimeters.

*Bloom quantity.*—Considered abundant, approximately 35 to 40 flowers per meter, with a good distribution and a high rate of fruit set.

*Flower bud frequency.*—Generally 2 flower buds appear per node, occasionally 1.

*Petal size.*—Generally. — Considered small. Length: Generally between 11.0 and 14.0 millimeters. Width: Generally 10.0 to 11.0 millimeters.

*Petal form.*—Round-shaped.

*Petal count.*—Generally 5.

*Petal texture.*—Smooth, soft and glabrous.

*Petal color.*—Both surfaces of the petal are colored with a purple Pink (RHS Red Purple 61 B to RHS Red Purple 61 C) when young, becoming slightly darker until the end of blooming.

*Fragrance.*—Sweet.

*Petal claw.*—Form. — The claw is considered to have a triangular form, slightly narrow at the base. Length. — Approximately 2.0 millimeters. Width. — Approximately 1.0 millimeter. Color. — Purple red (RHS Red Purple 73 B to RHS Red Purple 73 C).

*Petal margins.*—Generally considered slightly wavy.

*Petal apex.*—Generally. — The petal apices are generally round-shaped, curved.

*Flower pedicel.*—Length. — Considered medium to large and having an average length of approximately 3.0 millimeters. Diameter. — Considered average, approximately 1.5 to 2.0 millimeters. Color. — Yellow Green (RHS Yellow Green N144 A to RHS Yellow Green N144 B).

*Calyx.*—Internal surface texture. — Smooth and glabrous. Color. — The inner surface of the calyx is golden orange mat (RHS Greyed Red 178 C to RHS Greyed Red 178 D). The outer surface of the calyx is considered of purple-brown (RHS Greyed Purple 183 A to RHS Greyed Purple 183 C or RHS Greyed Purple 187 B) color and yellow green near the base (RHS Yellow Green 144 A to RHS Yellow Green 144 B).

*Sepals.*—Surface texture. — The outer surface has a short, fine pubescent texture. Size. — Average. Length. — Approximately between 6.0 and 7.0 millimeters. Width. — Approximately between 5.0 and 6.0 millimeters. Form. — Conic and round at the top. Color. — Both sides of sepals are colored with a matt Red (RHS Greyed Purple 183 A to RHS Greyed Purple 183 C or RHS Grey Purple 187 B).

*Average number of stamens per flower.*—Approximately 43 to 49 stamens per flower.

*Anthers.*—Generally. — Medium in length. Color. — At an early stage of maturity, anthers are colored orange yellow (RHS Yellow Orange 16 A to RHS Yellow Orange 16 B) or orange red (RHS Red Group N34 A or RHS Greyed Red Group 178 A). The color may evolve with maturity to turn in a yellow color.

*Pollen production.*—Pollen is abundant, and has a yellow color (RHS Yellow Orange 17 B to RHS Yellow Orange 17 C) which may evolve with maturity. The present variety is considered auto-fertile (self-pollinating).

*Filaments.*—Size. — Medium length, between 10.0 to 15.0 millimeters in length. Filaments length is generally the same or slightly higher than the pistil's length. Color: Considered white (RHS White N155 D) to light pink (RHS Red Purple 62 C to RHS Red Purple 62 D). The color may become darker during the blooming.

*Pistil.*—Number. — Usually 1. Generally. — Average in size. Length. — Approximately 16.0 to 20.0 millimeters including the ovary. Generally equal to stamen length, if not slightly smaller. Color. — Considered a very pale green (RHS Yellow Green Group 151 D). The color evolves during the blooming, becoming more light (RHS Yellow Green Group 150 D) and sometimes very slightly pink (RHS Red Group 36 D) at the end of blooming. Ovary. — The pubescence is absent.

Fruit:

*Maturity when described.*—Very firm in ripe conditions (shipping ripe).

*Date of first picking.*—Jun. 16, 2011.

*Date of last picking.*—The date of harvest varies slightly with the prevailing climatic conditions. The 'NECTAFLASH' variety has an early to medium date of picking, and a grouped maturity. The maturity is generally grouped within only one week and the harvest is generally performed in two runs. Last known picking times carry on Jun. $16^{th}$ to Jun. 20, 2011, then Jun. $28^{th}$ to Jul. 4, 2012 and then Jul. $2^{nd}$ to Jul. 10, 2013.

*Size.*—Generally. — Homogeneous in size. Considered medium. Average cheek diameter: Approximately 63.0 to 68.0 millimeters. Average axial diameter: Approximately 62.0 to 66.0 millimeters.

*Typical weight.*—Generally about 160.0 grams. This characteristic is high dependent upon the prevailing cultural practices, and therefore is not particularly distinctive of the variety.

*Fruit form.*—Generally. — Very round and regular, not pointed. The fruit is generally uniform in symmetry, viewed from the suture's plane.

*Suture.*—Fruit suture: Wide-mouthed and slightly marked, extending from the base to the apex. No apparent callousing or stitching exists along the suture line. Not pointed. Color. — The suture has generally a similar color to the whole fruit color, a luminous dark red (RHS Greyed Red 187 A to RHS Greyed Red 187 B).

*Ventral surface.*—Form. — Smooth.

*Apex.*—Non-prominent, generally slightly depressed.

*Base.*—Semi-flared, shallow.

*Stem cavity.*—Average depth of the stem cavity is about 9.0 millimeters. Average width is about 12.0 millimeters.

*Fruit skin.*—Thickness. — Considered very thick and strong, and the adherence of skin to flesh is strong to medium, depending on the fruit maturity. Texture. — Glabrous. Taste. — Semi-sweet, aromatic, with a high level of sugars. Tendency to crack. — None observed.

*Color.*—Blush color. — This blush color is a luminous dark red (RHS Greyed Purple 187 A to RHS Greyed Purple 187 B). The dark red blush covers 95% to 100% of the fruit skin surface. The percentage of the blush on the fruit skin surface can vary, and is generally dependant upon the prevailing conditions under which the fruit was grown. Ground color. — The ground color covers at the most 5 percent of the fruit skin surface, and is considered orange (RHS Orange Red N34 A).

*Fruit stem.*—Size: Medium in length, approximately 7.0 to 8.0 millimeters. Diameter: Approximately 4.0 millimeters. Color: Pale green (RHS Yellow Green 145 A to RHS Yellow Green 145 B).

*Flesh.*—Ripens. — Very homogenously, slowly. The flesh has a long shelf life. Texture. — Very firm, very dense, crunchy, melting, juicy at harvest maturity stage. Fibers. — Not fibrous. Aroma. — Pronounced. Eating quality. — Considered very good, aromatic and with a high level of sugars. Flavor. — Considered semi-sweet. The Brix is generally between 14.0 and 16.0 and acidity comprised between 6 and 9 meq/100 ml. Juice. — Very juicy at complete maturity. Brix. — Generally between 14.0 and 16.0 degrees. This characteristic varies slightly with the number of fruit per tree; prevailing cultural practices; and the surrounding climatic conditions. Flesh color. — The flesh is considered orange yellow (RHS Yellow Orange 16 A to RHS Yellow Orange 16 B) usually with a red pigmentation (RHS Orange Red 53 B) near the fruit's skin.

Stone:

*Type.*—Clingstone, more or less adherent depending on the fruit maturity.

*Size.*—Considered medium for the variety. The stone size varies significantly depending upon the tree vigor, crop load and prevailing growing conditions. Length: Approximately 28.0 to 30.0 millimeters. Width: Approximately 21.0 to 23.0 millimeters. Diameter: Approximately 16.0 to 18.0 millimeters.

*Form.*—Elliptic.

*Base.*—Straight.

*Apex.*—Shape. — The stone apex is short, pointed.

*Stone cavity.*—Considered medium size, with an ovate-form and dimensions corresponding to the stone's dimensions.

*Stone surface.*—Surface texture. — The pit is transversely furrowed on its entire surface. Furrows are more pronounced toward the apex. The stone is pitted toward the base. Relief is prominent generally and present basally. Ridges. — The surface texture is generally characterized by more prominent ridges along the ventral edges and is more prominent at the apical tip.

*Ventral edge.*—Width. — Considered small to medium, and having a dimension of approximately 2.0 millimeters at mid-suture.

*Dorsal edge.*—Shape. — Grooved.

*Stone color.*—The color of the dry stone is generally considered orange brown (RHS Greyed Orange 164 B to RHS Greyed Orange 164 C).

*Tendency to split.*—Splitting is very low or absent, depending on climatic conditions between blooming period and stone hardening.

*Kernel.*—Size. — The kernel is considered medium. Length. — Approximately 15.0 millimeters. Width. — Approximately 9.0 millimeters. Thickness. — Approximately 3.0 millimeters. Form. — Considered flattened and elliptic. Pellicle. — The pellicle of the kernel has a short pubescence. Color. — The kernel skin is considered orange brown (RHS Greyed Orange 164 A) with slightly darker streaks (RHS Greyed Orange N 167 B). The almond, which is the seed of the kernel, is white (RHS White 155 B) and has a bitter tasting. The kernel and its embryo are mature at the time of fruit maturity.

Use: The subject variety 'NECTAFLASH' is considered to be a yellow nectarine tree of early to medium season of maturity, and which produces fruits that are considered firm, attractively colored with a very luminous dark red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

Keeping quality: Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

Shipping quality: Considered very good. The fruit of the new yellow nectarine variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

Resistance to insects and disease: No particular susceptibilities were noted. The present variety is not very sensitive to powdery mildew, or conservation diseases and decay due to its thick and strong skin.

Although the new variety of nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

We claim:

1. A new and distinct variety of yellow nectarine tree as illustrated and described, characterized by fruits with high eating quality and very long shelf life without alteration before and after harvesting, with a semi-sweet yellow flesh, with a red pigmentation near the fruit's skin, and an attractive luminous and homogenous skin with a high percentage of dark red blush on skin surface, on an orange background.

* * * * *